United States Patent [19]

Yoshino

[11] Patent Number: 5,491,257
[45] Date of Patent: Feb. 13, 1996

[54] FLUORINE-CONTAINING AROMATIC COMPOUNDS

[75] Inventor: Norio Yoshino, Mitaka, Japan

[73] Assignee: Daikin Industries, Ltd., Osaka, Japan

[21] Appl. No.: 213,159

[22] Filed: Mar. 15, 1994

[30] Foreign Application Priority Data

Sep. 13, 1993 [JP] Japan ................................. 5-252578

[51] Int. Cl.$^6$ ................................................ C07C 309/24
[52] U.S. Cl. ................................ 562/41; 562/459; 562/24
[58] Field of Search ................................................ 562/41

[56] References Cited

PUBLICATIONS

Katsuta, CA:96-68623t (1982).
"Hybrid Surfactants Containing Separte Hydrocarbon and Fluorocarbon Chains", Wen Guo, et al, *J. Phys. Chem.*, 1992, 96, pp. 6738-6742.

*Primary Examiner*—Nicky Chan
*Attorney, Agent, or Firm*—Loeb and Loeb

[57] ABSTRACT

The present invention provides a compound which has a fluoroalkyl group, a lipophilic group (an alkyl group) and a hydrophilic group in the same molecule.

7 Claims, No Drawings

FLUORINE-CONTAINING AROMATIC COMPOUNDS

The present invention relates to fluorine-containing aromatic compounds and in particular to those which increase the dispersibility to and compatibility of inorganic and organic materials with fluorine materials such as fluorine oils and fluorine plastics which show high performance in many fields. Further, the present invention, also relates to precursor compounds thereof.

Because conventional surfactants have had in the same molecule only two types of functional groups such as a lipophilic group and a hydrophilic group, a fluoroalkyl group and a hydrophilic group, or a lipophilic group and a fluoroalkyl group, for example it is difficult to disperse a fluorine compound into a stable dispersion system of inorganic materials/organic materials. However, the use of a surfactant having three types of functional groups of a lipophilic group, a fluoroalkyl group and a hydrophilic group in the same molecule can make it possible stably to disperse a fluorine material into a stable dispersion system of inorganic materials/organic materials and to extend the application field of fluorine materials having specific properties.

B. M. Fung et al disclose a synthesis of

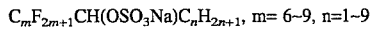

$C_mF_{2m+1}CH(OSO_3Na)C_nH_{2n+1}$, m= 6~9, n=1~9 which is a surfactant having a fluoroalkyl group, a lipophilic group and a hydrophilic group in the same molecule (J. Phys. Chem. 96 6738~6742, 1992). However, the compounds are susceptible to being hydrolized by humidity in air and are immediately decomposed unless stored at a low temperature and dry state, hence extremely unstable.

It is the object of the present invention to provide a compound which is stable and modifies the surface of inorganic materials or organic materials to make possible the adhesion, filling or dispersion of such materials to various fluorine materials and further modifies the surface of both inorganic materials and organic materials to make possible their adhesion, filling or dispersion to various fluorine materials.

The present invention provides a compound which has a fluoroalkyl group, a lipophilic group (an alkyl group) and a hydrophilic group in the same molecule.

The above-mentioned compounds of the present invention are represented by for example formula (III): $RfC_6H_4COCHXR$ wherein Rf is a fluoroalkyl group having 1 to 20 carbon atoms; X is $SO_3M$, COOM or $PO_3M_2$; M is an alkali metal or $NH_4$; and R is an alkyl group having 1 to 20 carbon atoms. Preferable Rf includes for example perfluoromethyl, perfluoroethyl, perfluoropropyl, perfluorobutyl, perfluorohexyl, perfluorodecyl, perfluorododecyl, perfluoropentadecyl, perfluoroheptadecyl, perfluoroeicosyl and the like. Preferable R includes for example methyl, ethyl, propyl, butyl, hexyl, decyl, dodecyl, pentadecyl, heptadecyl, eicosyl and the like.

Compounds (III) described above can be obtained by for example reacting a fluorine-containing aromatic compound represented by the formula (II): $RfC_6H_4COCH_2R$ with sulfur trioxide ($SO_3$), carbon dioxide ($CO_2$), phosphorus oxychloride ($POCl_3$) or the like followed by addition of water and neutralization of the resulting aqueous layer with an alkali metal compound, ammonia or the like. Examples of useful alkali metal compounds are sodium hydroxide and potassium hydroxide. Preferably, the reaction is usually carried out in the presence of a solvent which for example includes dichloroethane, dioxane, chloroform and the like. The reaction temperature is preferably in the range of 0° C. to room temperature and about 2 to 5 hours are sufficient as the reaction time.

Next, compounds (II) described above can be obtained by coupling an aromatic compound represented by the formula (I): $IC_6H_4COCH_2R$ with a fluoroiodide compound represented by the formula; RfI wherein Rf is as defined above. Preferably, the reaction is performed in the presence of copper powder, zinc powder, cadmium, magnesium and the like. Further, preferably the reaction is usually carried out in the presence of a solvent, which for example includes dimethyl sulfoxide, dimethylformamide and the like. The reaction temperature is preferably in the range of 100° to 150° C. and about 16 to 30 hours are sufficient as the reaction time. Compounds (II) wherein $Rf=CF_3$ and $R=CH_3$, or $Rf=CF_8$ and $R=C_2H_5$ are excluded from those defined above.

Compound (I) described above can be obtained by a Friedel-Crafts reaction of an acid chloride represented by the formula: $RCH_2COCl$ wherein R is as defined above with iodobenzene ($C_6H_6I$). The reaction is preferably carried out in the presence of $AlCl_3$, $AlBr_3$, $FeCl_3$, $SnCl_4$, $TiCl_4$, $ZnCl_2$ or the like. Further, it is preferably performed in the presence of a solvent, which for example includes carbon disulfide, nitromethane, acetonitrile, methylene chloride, nitrobenzene and the like. The reaction is preferably carried out under reflux and about 16 to 24 hours are sufficient as the reaction time. Compounds (I) wherein $R=CH_3$, $C_6H_{13}$ or $C_8H_{17}$ are excluded from those defined above.

The present invention also relates to compounds (I) and (II) described above. The above compounds (I) to (III) of the present invention can be usually purified by known means such as extraction, filtration, distillation, recrystallization, and column chromatography.

Fluorine-containing aromatic compounds (III) of the present invention can lower surface tension with its very low concentration. In the present invention when the surface of inorganic materials and organic materials which are incompatible with fluorine materials such as fluorine oils and fluorine plastics is treated with a compound (III) of the present invention, the surface of these materials can be densely coated with fluoroalkyl groups and thus the treated inorganic materials and organic materials become compatible with fluorine materials such as fluorine oils and fluorine plastics, and come to have a stable dispersibility. Further because compounds (III) of the present invention have a fluoroalkyl group, a lipophilic group and a hydrophilic group in the same molecule, they can also mingle an inorganic material, an organic material and a fluorine material at once. Namely, for example, a fluorine material can be dispersed in a dispersion system of an inorganic material and an organic material. Thus, compounds (III) of the present invention are useful as surfactants, surface-modifying agents for many and various materials, binders and the like.

The compounds of the present invention can be used in various applications depending on the types, for example in the following field. However the applications are not limited to the below-mentioned ones.

Namely, they have applications as water repellent agents, oil repellent agents, release agents, stain-proofing agents, rust preventives, detergents, cleaners, waxes, dyes, film coating agents, foamed products, anti clouding agents, flotation reagents, oil/water separating agents, solubilization agents, frothing agents, foam stabilizers, fire-extinguishing foam agents, oil-gathering agents, penetrants, evaporation inhibitors, leveling agents, emulsion breakers, dyeing assistants, plating additives, extreme pressure additives, lubricants, fire retardants, emulsifying agents for the emulsion polymerization of fluorine resins, germicide, disinfectant, acid liquid additives, softening agents, fire extinguishments for oil fires, textile finishing agents, metal-containing surface treating agents, antistatic agents, and resin modifying agents for incorporation; and further have applications in coloration of fluorine resins or fibres, and fluorine coating compositions by filling color pigments, etc., filling of hydrated alumina or calcium carbonate to fire retarding polymers, dispersion of iron oxide in magnetic coating compositions for magnetic recording media, dispersion of iron oxide in magnetic fluids, dispersion of aluminum in electromagnetic wave shielding agents, missile therapy drugs which are a combination of sustained release preparation and a magnetic fluid, cancer treating drugs which are a combination of a radioactive isotope with a short half-life period and a magnetic fluid, magnetic toners, surface-protecting-film forming agents and modification of fluorine rubbers.

The present invention will be described in detail by the following Examples.

EXAMPLES 1 TO 3

Compounds (I) represented by the formula: $IC_6H_4COCH_2R$ were obtained by using acid chlorides ($RCH_2COCl$), iodobenzene, aluminum chloride and carbon disulfide shown in Table 1. Into a 500 ml round-bottom flask was placed a stirring rod. Aluminum chloride was weighed out and placed in the flask. The flask was equipped with a reflux condenser and a pressure equalization dropping funnel and the air in the flask was replaced with nitrogen. Next, carbon disulfide was added by a syringe to suspend the aluminum chloride. Acid chloride and iodobenzene were slowly added dropwise in turn under ice-cooling through the pressure-equalization dropping funnel. The reaction mixture was stirred at room temperature for 1 hour and heated under reflux for 16 hours. The reaction liquid was poured into cold water and the resulting organic layer was washed with dilute hydrochloric acid and washed with water till the washing becomes neutral followed by washing with an aqueous solution of sodium thiosulfate and water. The solvent in the organic layer was removed by distillation at a reduced pressure. The residue was distilled at a reduced pressure and the distillate was dissolved in diethyl ether, and washed with an aqueous solution of sodium thiosulfate and water. The diethyl ether was distilled off at a reduced pressure to obtain the desired compounds (I).

TABLE 1

| Ex. | $RCH_2COCl$ (g) | | $C_6H_5I$ (g) | $AlCl_3$ (g) | $CS_2$ (ml) | yield (%) | bp (°C./Pa) | mp (°C.) |
|---|---|---|---|---|---|---|---|---|
| 1 | R = $C_2H_5$, | 24.8 | 47.5 | 31.0 | 100 | 69.3 | 94.0/40 | 58.5 |
| 2 | R = $C_4H_9$, | 25.6 | 37.3 | 24.6 | 80 | 73.2 | 83.5/25 | 62.4 |
| 3 | R = $C_6H_{13}$, | 24.7 | 31.7 | 20.1 | 64 | 71.9 | 113.5/39 | 64.0 |

EXAMPLES 4 TO 10

Compounds (II) represented by the formula: $RfC_6H_4COCH_2R$ were obtained by using compounds represented by the formula (I): $IC_6H_4COCH_2R$, a fluoroiodide compound (RfI), copper powder and dimethyl sulfoxide (DMSO) shown in Table 2. Into a 200 ml round-bottom flask was placed a stirrer rod. $IC_6H_4COCH_2R$(I) is weighed out and copper powder was taken in a dry bag. A reflux condenser was attached to the flask. DMSO and RfI were added by a syringe. The reaction was carried out at 120° C. for 16 hours. After reaction, water was added, and separated copper iodide and residual copper powder were removed by suction filtration. The filtrate was extracted with diethyl ether and the diethyl ether layer was washed with water. The diethyl ether was removed by distillation at a reduced pressure. The residue was distilled at a reduced pressure and recrystallized from methanol to obtain the desired compounds (II). All the products of Examples 4 to 6 and 10 are solid and all the products of Examples 7 to 9 are liquid.

TABLE 2

| Ex. | $IC_6H_4COCH_2R$ (g) | | RfI (g) | | copper powder (g) | DMSO (ml) | yield (%) | bp (°C./Pa) | mp (°C.) |
|---|---|---|---|---|---|---|---|---|---|
| 4 | R = $C_2H_5$, | 15.6 | Rf = $C_6F_{13}$, | 25.7 | 15.1 | 100 | 86.0 | 88.5/49 | 36.6 |
| 5 | R = $C_4H_9$, | 16.9 | Rf = $C_6F_{13}$, | 25.6 | 19.2 | 100 | 70.1 | 86.5/21 | 43.5 |
| 6 | R = $C_6H_{13}$, | 18.6 | Rf = $C_6F_{13}$, | 25.4 | 16.7 | 100 | 67.0 | 102.0/27 | 49.7 |
| 7 | R = $C_2H_5$, | 19.9 | Rf = $C_4F_9$, | 27.8 | 24.8 | 120 | 68.3 | 58.5/24 | — |
| 8 | R = $C_4H_9$, | 21.8 | Rf = $C_4F_9$, | 27.0 | 18.9 | 120 | 66.3 | 72.5/27 | — |
| 9 | R = $C_6H_{13}$, | 23.6 | Rf = $C_4F_9$, | 26.4 | 22.1 | 120 | 50.0 | 72.2/20 | — |
| 10 | R = $C_6H_{13}$, | 9.9 | Rf = $C_8F_{17}$, | 19.6 | 12.1 | 50 | 58.6 | 109.5/40 | 42–45 |

EXAMPLES 11 TO 17

Compounds (III) represented by the formula: $RfC_6H_4COCH(SO_3Na)R$ were obtained by using compounds represented by the formula (II): $RfC_6H_4COCH_2R$, sulfur trioxide ($SO_3$), dichloroethane and dioxane shown in Table 3. Into a 100 ml round-bottom flask was placed a stirring rod. A pressure equalization dropping funnel was attached to the flask and the air in the flask was replaced with nitrogen. Dichloroethane and sulfur trioxide were weighed out and placed in the round-bottom flask and dioxane was slowly added dropwise under ice cooling through the pressure-equalization dropping funnel. A compound (II) was dissolved in dichloroethane under a nitrogen atmosphere and the solution was slowly added dropwise at room temperature through the pressure-equalization dropping funnel. The resulting mixture was stirred at room temperature for 3 hours and water was added, the aqueous layer was neutralized with an aqueous solution of sodium hydroxide and the water was evaporated to separate out a solid. The solid was washed with methanol to obtain the desired compounds (III). All the products are white powders.

TABLE 3

| Ex. | RfC$_6$H$_4$COCH$_2$R (g) | | SO$_3$ (g) | dichloro-ethane (ml) | dioxane (g) | yield (%) |
|---|---|---|---|---|---|---|
| 11 | Rf = C$_6$F$_{13}$, | R = C$_2$H$_5$, | 9.36 | 2.13 | 6 | 2.33 | 34.6 |
| 12 | Rf = C$_6$F$_{13}$, | R = C$_4$H$_9$, | 9.06 | 1.47 | 6 | 1.61 | 85.8 |
| 13 | Rf = C$_6$F$_{13}$, | R = C$_6$H$_{13}$, | 7.84 | 1.24 | 6 | 1.37 | 79.3 |
| 14 | Rf = C$_4$F$_9$, | R = C$_2$H$_5$, | 7.3 | 1.87 | 6 | 2.02 | 54.3 |
| 15 | Rf = C$_4$F$_9$, | R = C$_4$H$_9$, | 8.8 | 2.20 | 6 | 2.32 | 75.0 |
| 16 | Rf = C$_4$F$_9$, | R = C$_6$H$_{13}$, | 8.6 | 1.89 | 6 | 2.10 | 38.1 |
| 17 | Rf = C$_8$F$_{17}$, | R = C$_6$H$_{13}$, | 6.2 | 1.73 | 6 | 2.05 | 38.2 |

Test Example 1

Water (22.98 g), n-octane (1.00 g), Demnum S-20 (a fluorine oil manufactured by Daikin Industries, Ltd.) (1.00 g), and the compound represented by the formula: C$_6$F$_{13}$C$_6$H$_4$COCH(SO$_3$Na)C$_4$H$_9$ (0.02 g) prepared in Example 12 were mixed and ultrasonic wave was irradiated for 3 minutes with a ultrasonic wave homogenizer to obtain a solution wherein the components were homogeneously dispersed and consequently three components of an inorganic material, an organic material and a fluorine material were successfully compatibilized.

Comparative Test Example 1

Water (22.98 g), n-octane (1.00 g), Damhum S-20 (1.00 g), and a fluorine-containing surface active agent DS-102 (a perfluoroalkylcarboxylic acid salt manufactured by Daikin Industries, Ltd.) (0.02 g) were mixed and ultrasonic wave was irradiated for 3 minutes with a ultrasonic wave homogenizer. However a solution wherein the components were homogeneously dispersed was not obtained and consequently three components of an inorganic material, an organic material and a fluorine material could not be compatibilized.

Test Example 2

The comparison of the cmc (critical micelle concentration) and surface tension of aqueous solutions of each of the compound represented by the formula: C$_6$F$_{13}$CH$_4$COCH(SO$_3$Na)C$_2$H$_5$ obtained in Example 11, the compound represented by the formula: C$_6$F$_{13}$C$_6$H$_4$COCH(SO$_3$Na)C$_4$H$_9$ prepared in Example 12, the compound represented by the formula: C$_6$F$_{13}$C$_6$H$_4$COCH(SO$_3$Na)C$_6$H$_{13}$ prepared in Example 13, the compound represented by the formula: C$_4$F$_9$C$_6$H$_4$COCH(SO$_3$Na)C$_2$H$_5$ prepared in Example 14, the compound represented by the formula: C$_4$F$_9$C$_6$H$_4$COCH(SO$_3$Na)C$_4$H$_9$ prepared in Example 15, the compound represented by the formula: C$_4$F$_9$C$_6$H$_4$COCH(SO$_3$Na)C$_6$H$_{13}$ prepared in Example 16, a hydrocarbon surfactant [H(CH$_2$)$_8$SO$_3$Na], and a fluorine-containing surfactant [F(CF$_2$)$_8$SO$_3$Na] revealed that the six compounds obtained in Examples 11 to 16 have very excellent properties as a surfactant because their values of cmc concentration and surface tension are smaller relative to those of conventional hydrocarbon and fluorine-containing surfactants. The results are shown in Table 4.

TABLE 4

| No. | compound | cmc × 10$^{-3}$ (mol/l) | surface tension (mN/m) | Kraft point (°C.) |
|---|---|---|---|---|
| 1 | C$_6$F$_{13}$C$_6$H$_4$COCH(SO$_3$Na)C$_2$H$_6$ | 0.83 (25) | 21.5 (25) | <0 |
| 2 | C$_6$F$_{13}$C$_6$H$_4$COCH(SO$_3$Na)C$_4$H$_9$ | 0.23 (25) | 20.4 (25) | 15 |
| 3 | C$_6$F$_{13}$C$_6$H$_4$COCH(SO$_3$Na)C$_6$H$_{13}$ | 0.055 (50) | 18.0 (50) | 48 |
| 4 | C$_4$F$_9$C$_6$H$_4$COCH(SO$_3$Na)C$_2$H$_5$ | 8.2 (25) | 25.0 (25) | <0 |
| 5 | C$_4$F$_9$C$_6$H$_4$COCH(SO$_3$Na)C$_4$H$_9$ | 3.5 (25) | 22.0 (25) | <0 |
| 6 | C$_4$F$_9$C$_6$H$_4$COCH(SO$_3$Na)C$_6$H$_{13}$ | 1.2 (25) | 20.0 (25) | 20 |
| 7 | H(CH$_2$)$_8$SO$_3$Na | 140 (40)[1] | 44.0 (40)[1] | |
| 8 | F(CF$_2$)$_8$SO$_3$Na | 8.5 (75)[1] | 40.5 (25)[1] | |

Note: [1]H. Kitahara, Y. Tamai, S. Hayano, and I. Hara, "Surface Active Agents - Properties · Applications · Chemical ecology", Kodan-sha, page 18 (1990).
*The numbers in parentheses show a temperature (°C.) when measured.

The fluorine-containing aromatic compounds (III) of the present invention have hardly been known, which have a fluoroalkyl group, a lipophilic group and a hydrophilic group in the same molecule. Because fluorine-containing aromatic compounds (III) of the present invention can lower surface tension of its solution with their very low concentration, they can modify inorganic agents and organic agents used together with fluorine agents such as fluorine oils or fluorine resins to improve the compatibility of the former agents with the latter fluorine agents and then can be widely used as an auxiliary for providing composite materials of fluorine compounds.

We claim:

1. A compound represented by the formula (III):

$$R_fC_6H_4COCHXR \tag{III}$$

wherein $R_f$ is a fluoroalkyl group having 1 to 20 carbon atoms; X is $SO_3M$; M is an alkali metal or $NH_4$; and R is an alkyl group having 1 to 20 carbon atoms.

2. The compound according to claim 1, wherein Rf is a fluoroalkyl group selected from the group consisting of perfluoromethyl, perfluoroethyl, perfluoropropyl, perfluorobutyl, perfluorohexyl, perfluorodecyl, perfluorododecyl, perfluoropentadecyl, perfluoroheptadecyl and perfluoroeicosyl.

3. The compound according to claim 2, wherein $R_f$ is perfluorohexyl.

4. The compound according to claim 1, wherein R is an alkyl group selected from the group consisting of methyl, ethyl, propyl, butyl, hexyl, decyl, dodecyl, pentadecyl, heptadecyl and eicosyl.

5. The compound according to claim 4, wherein R is ethyl.

6. The compound according to claim 1, wherein X is $SO_3Na$.

7. A compound of the formula $C_6F_{13}C_6H_4COCH(SO_3Na)C_2H_5$.

* * * * *